United States Patent [19]

Gross

[11] Patent Number: 5,395,345
[45] Date of Patent: Mar. 7, 1995

[54] ASPIRATING SYRINGE

[75] Inventor: James R. Gross, Wareham, Mass.

[73] Assignee: The Kendall Company, Mansfield, Mass.

[21] Appl. No.: 186,944

[22] Filed: Jan. 27, 1994

[51] Int. Cl.$^6$ ................................................ A61M 5/00
[52] U.S. Cl. .................................... 604/187; 604/218; 128/763
[58] Field of Search ............... 604/187, 218, 220, 221, 604/223, 230; 128/763–765

[56] References Cited

U.S. PATENT DOCUMENTS

| | | | |
|---|---|---|---|
| 4,121,739 | 10/1978 | Devaney et al. | 604/222 X |
| 4,664,128 | 5/1987 | Lee | 604/187 |
| 4,997,423 | 3/1991 | Okuda et al. | 604/230 |

Primary Examiner—John D. Yasko
Attorney, Agent, or Firm—Alvin Isaacs

[57] ABSTRACT

The invention features an aspirating syringe which includes a plastic syringe barrel having an exterior wall and an inner surface, and leading and trailing ends. The inner surface and ends define a hollow interior chamber and a predetermined volume. The leading end of the barrel has an opening extending through a hub and the trailing end terminates at an outer rim. The syringe also includes a plastic plunger slidingly operative in the barrel. The leading, i.e., sealing, end of the plunger helps to define the hollow interior chamber and the predetermined volume. The plunger extends longitudinally within and beyond the barrel trailing end and is movable in the barrel inwardly toward the leading end and outwardly away from the leading end, thereby varying the predetermined volume of and pressure within the barrel interior chamber. The plunger also has a sealing end receivable inside the barrel to substantially seal the hollow interior chamber and a thumb-receiving end outside the barrel. The syringe includes a finger grip member extending perpendicular from the barrel trailing end. An outward biasing means is coiled around the plunger between the barrel trailing end and the plunger thumb-receiving end to bias the plunger outwardly from the syringe barrel upon advancement of the plunger into the barrel.

5 Claims, 2 Drawing Sheets

ASPIRATING SYRINGE

FIELD OF THE INVENTION

The invention relates to syringes in general and in particular to aspirating syringes.

BACKGROUND OF THE INVENTION

In medical applications, an aspiration device is one which applies pressure or partial vacuum to draw a fluid or sample into a syringe or into an attached needle lumen. Such devices are also useful for securing specimens from palpable and non-palpable lesions found in the thyroid, breast, lymph nodes, prostate, liver, kidney, lung and pancreas for histologic and cytologic examination.

The simplest and most widely used prior art aspirating device is a conventional, plastic hypodermic syringe of the type having a hollow needle opening into a syringe barrel and a plunger for varying the volume and pressure inside the barrel. In use, negative pressure is created by drawing back on the plunger. This requires two hands, one to hold the syringe barrel and one to withdraw the plunger, or, if the syringe incorporates finger and thumb rings, negative pressure is generated by the thumb flexing in opposition to the fingers.

In certain other procedures, thoracentesis for example, it is imperative that the tip of the needle be precisely located within the pleural space but not so deeply inserted as to cause puncture to the lung. Briefly, the aspiration needle is connected to a syringe, insuring that the plunger is fully inserted into the barrel of the syringe. The needle is inserted into the body and slowly advanced toward the pleural space. During this advancement, two hands are required to effect precise location of the needle tip within the pleural space. The syringe and needle are advanced into the body with one hand, while simultaneously pulling back on the syringe plunger with the other hand to create a vacuum within the syringe barrel and inside the needle. Entry of the needle into the pleural space is manifest by the pleural effusion flowing back into the syringe.

Accordingly, there is a need for an improved single-hand operated aspiration device for conducting medical procedures involving aspiration of bodily fluids. One object of the invention is to eliminate the necessity of manually aspirating the syringe so that both hands may be dedicated to the correct placement of the needle tip.

It is another object of the invention to provide a plastic syringe which has highly sensitive feel and low resistance, while at the same time offering the advantage of improved single-hand operation during aspiration procedures.

SUMMARY OF THE INVENTION

The invention features a syringe particularly useful for aspiration of fluid. The syringe includes a plastic syringe barrel having an exterior wall and an inner surface, and leading and trailing ends, the inner surface and ends defining a hollow interior chamber and a predetermined volume, the leading end having an opening extending through a hub, the trailing end terminating at an outer rim; a plastic plunger operative in the barrel through the barrel trailing end to define the hollow interior chamber and the predetermined volume, the plunger extending longitudinally within the barrel and being movable in the barrel inwardly toward the barrel leading end and outwardly away from the leading end, thereby varying the volume of and pressure within the barrel interior chamber, the plunger having a sealing end receivable inside the barrel to substantially seal the hollow interior chamber and a thumb-receiving end outside the barrel. The syringe includes a finger grip member attached to and extending perpendicular from the barrel trailing end. An outward biasing means is coiled around the plunger between the barrel trailing end and the plunger thumb-receiving end to bias the plunger outwardly from the syringe barrel upon advancement of the plunger into the barrel.

Due to the action of the outward biasing means, the device is especially suited for thoracentesis procedures where aspiration of bodily fluid is essential.

The syringe barrel trailing end includes an outer rim and the leading end is provided with a luer tip and an opening through the luer tip. The luer tip is designed to accommodate a needle which when attached to the luer tip provides for fluid communication between the syringe barrel of the device and the needle. The luer tip may also include a luer tip locking collar for securely attaching the needle to the syringe. The plunger is positioned in the barrel for changing the volume and pressure inside the barrel, thereby providing the necessary partial vacuum or negative pressure for aspiration as well as the positive pressure needed for expulsion of fluid. Control of movement of the plunger within the barrel is effected by the counteracting forces of the outward biasing means, e.g., a spring, which pushes against the trailing end of the syringe barrel at one end and against the trailing end of the plunger, and the thumb of the syringe user, which pushes against the trailing end of the plunger in opposing force with the outward biasing means.

The syringe also includes a finger grip member extending perpendicular from the barrel trailing end. The finger grip member may include two circular finger-receiving slots arranged such that one slot is placed opposite the other around the barrel. The circular finger-receiving slot may further include a curved finger receptacle abutting the slot such that the spring may be coiled by applying pressure to both the finger receptacles and the plunger thumb-receiving end.

Thus, according to the present invention, a disposable aspirating device for aspiration procedures including a plastic syringe and plunger/spring combination is provided.

A primary purpose of the device is to provide an improved method for conducting procedures involving needle aspiration. The device of the present invention requires only one hand to be operated effectively. The device allows precise control of the pressure applied while the needle is being inserted, while the needle is in the tissue, and while the needle is being retracted.

The present invention solves deficiencies found in the prior art. The device allows an operator to precisely control the application and cessation of pressure of the device with one hand during needle aspiration procedures while the user's other hand is free. Further, the simplicity of the invention lends itself to production as a disposable item, eliminating the need for costly and time consuming re-sterilization, maintenance and storage.

Other advantages of the invention include attachment of the syringe to the needle such that the plunger is positioned forward within the syringe barrel, at such time that the needle tip is occluded within the patient's body tissue, such that automatic aspiration is effected upon entry of the needle tip into the pleural space. Prior to entry of the needle tip into the pleural space, the plunger will remain forward in the barrel due to creation of a vacuum while the needle tip is within the body tissues. Appearance of pleural effusions within the syringe barrel would then signal the correct placement of the needle tip. Both hands can then be dedicated to advancing the needle to its precise and proper location.

In a preferred embodiment of the invention, the syringe is a low friction syringe designed to effect exceedingly low resistance between the plunger and inner surface of the syringe barrel during movement of the plunger within the barrel. The spring is wound around the plunger of the low resistance syringe such that it pushes against the trailing end of the syringe barrel at one end and against the thumb-receiving end of the plunger at the other end. Again, the user controls movement of the plunger by effecting thumb pressure against the thumb-receiving end of the plunger in opposing force with the spring. Highly sensitive movement of the plunger in the syringe may be effected using the spring/low resistance syringe combination due to the natural tendency of the low resistance syringe to respond to differential pressure between the pressure in the space into which the needle is inserted and the pressure within the syringe barrel. The gasket of the low resistance syringe confers the property of low resistance on the syringe. The gasket includes a body with forward and rearward ends and first and second annular flanges positioned circumferentially at the forward and rearward ends of the body, the flanges being separated by an annular space intermediate the body portion and the barrel inner surface, wherein each of the first and second flange further comprises a projection of reduced thickness relative to the thickness of the flange itself, each projection providing a contact point with the barrel inner surface when the plunger leading end is received in the barrel chamber and enabling frictional contact with the barrel inner surface during forward and rearward movement of the gasket. The frictional resistance between the plunger gasket and barrel inner surface is so low that a change in pressure inside the syringe barrel is communicated to the user by a corresponding movement of the plunger.

The invention also includes methods of aspirating bodily fluid or tissue using a syringe of the invention. Thus, the syringe is provided in operative association with a needle and arranged with pressure applied to the thumb-receiving end of the syringe such that the plunger is positioned well within the barrel; the needle is inserted into a patient; pressure on the thumb-receiving end is relieved enough to allow the syringe plunger to retract sufficiently to aspirate a specimen from the patient into the needle; and the needle is removed from the patient.

The method may also include the step of re-applying sufficient pressure to the thumb-receiving end of the syringe to eject the specimen from the needle.

Further features will become more fully apparent in the following description of the embodiments of this invention and from the appended claims.

DETAILED DESCRIPTION OF THE INVENTION

The present invention is an improved aspirating device designed for single-hand operation, e.g., in fine needle aspiration biopsy procedures. Particularly, the present invention provides an outward biasing means biased against the plunger trailing end and the syringe barrel trailing end to urge the plunger out of the barrel. The outward biasing means may include any means for urging the plunger out of the barrel, e.g., a coiled spring which is wound around the plunger. The outward biasing means allows for the precise application of negative and positive pressure within the syringe barrel.

Figure 1:
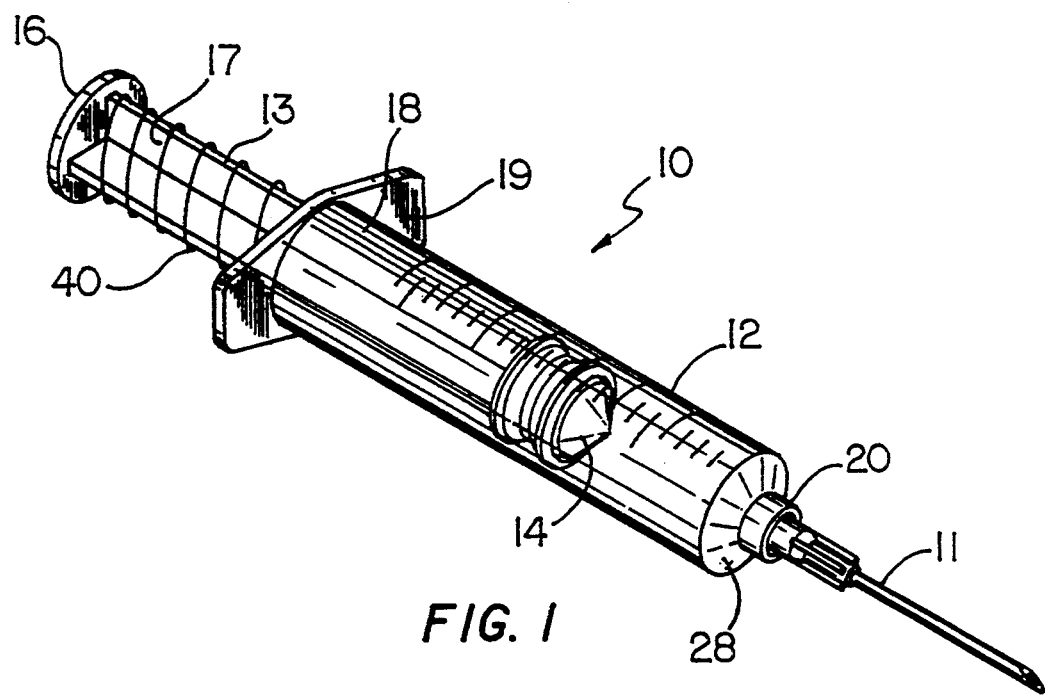
FIG. 1 is a perspective view of the device embodying the principles of the present invention.
Figure 2:
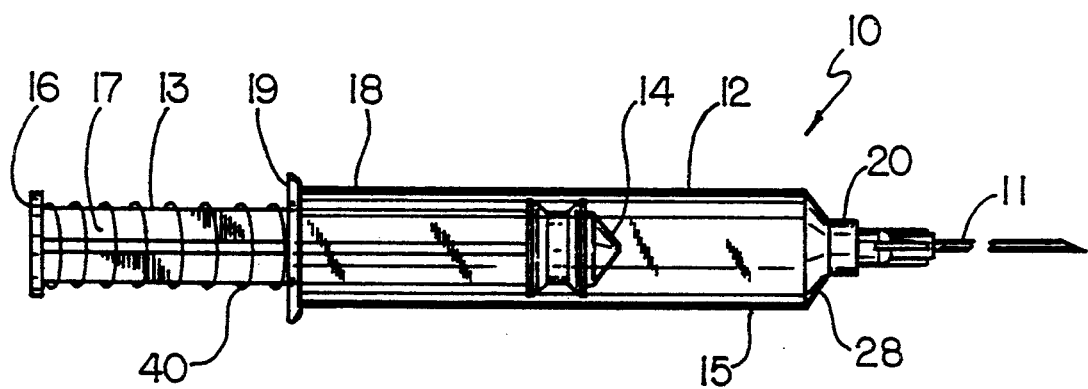
FIG. 2 is a side view of the device embodying the principles of the present invention.

A preferred embodiment of the present invention will be explained with reference to FIGS. 1 and 2, in which like elements are designated with like reference numbers. For ease of description, the ends of some of the components of the device described herein are referred to as leading and trailing; i.e., the leading end referring to the end which encounters the body first upon insertion or which is closer to the body during use.

In a preferred embodiment, an aspirating device 10 is provided and includes a syringe barrel 12, a plunger 13 operative in the barrel 12, and a spring 40 that is coiled around the plunger 13 and provides control of plunger 13 movement in barrel 12 as described herein. The aspirating device 10 when used in aspirating procedures will include a thin-walled hollow needle 11, the lumen of which opens through hollow needle 11 and into luer tip 20 of barrel 12 of the aspirating device 10.

The barrel of the aspirating device 10 has an exterior wall, interior wall, a leading end 28 and a trailing end 18. The walls and ends define a hollow interior chamber having a predetermined volume. Further, the barrel 12 includes a hub 20, an opening through the hub 20 and barrel 12 at the leading end 28.

The plunger 13 extends within and external to the barrel 12 and is operable therein. Particularly, the plunger 13 has one end inside the barrel 12 and another end external to the barrel 12. At the end of the plunger 13 which is outside barrel 12, the plunger 13 is provided with a thumb-receiving end 16. Spring 40 is wrapped around plunger 13 between the trailing end 18 of barrel 12 and the thumb-receiving end 16 of plunger 13. The plunger 13 has a gasket 14 at the end inside the barrel 12 which interacts with the walls of the barrel 12 to effectively create a chamber 15 inside the barrel 12. The gasket 14 consists of material different than the barrel, such as rubber, so that the interior plunger end is sealingly received within the barrel 12. The bias which the spring 40 creates against the trailing end 18 of barrel 12 at one end of spring 40 and the thumb-receiving end 16 of plunger 13 at the other end of spring 40 allows for variable control of the volume and pressure within barrel chamber 15. This control is even more effective when the user applies thumb pressure to the thumb-receiving end 16 of plunger 13, thus creating an opposing force against the bias of spring 40. When plunger 13 is positioned in the barrel 12, the only opening into the interior of the barrel is provided by the opening at the leading end 28. When needle 11 is attached at hub 20, the only opening into the barrel 12 is provided by the lumen of needle 11.

Figure 3:
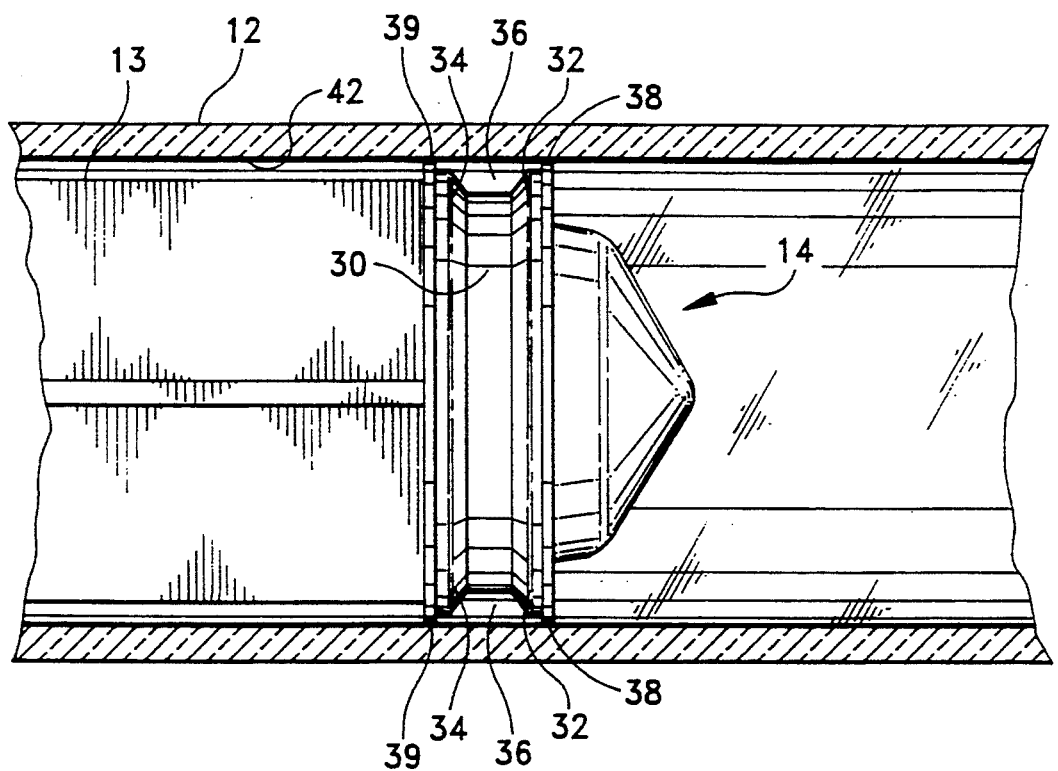
FIG. 3 is a fragmentary sectional view of another embodiment of the syringe of FIG.1.

An alternative embodiment of a syringe of the invention is shown in FIG. 3. Referring to FIG. 3, the gasket portion 14 within the barrel of the syringe is shown in cut-away. Gasket 14 includes main body portion 30 which is secured to the plunger 13. Gasket 14 has first and second annular flanges 32,34, respectively. Flanges 32,34 are tapered at their sides and, together with inner surface 42 of barrel 12, define inter-flange space 36.

The property of low resistance in this syringe embodiment of the invention, described fully in the concurrently filed U.S. Ser. No. 08/187,034 entitled "Low Friction Syringe", owned by the same assignee and hereby incorporated by reference, is obtained by virtue of the presence of projections 38,39 extending from flanges 32,34, respectively and which have a reduced thickness relative to the thickness of flange 32 or 34. Projections 38,39 come into only slight contact with the inner surface 42 of the syringe barrel 12. Projections 38,39 may be of any shape suitable for creating drag with respect to the inner surface of barrel 12, e.g., in cross-section, a square, circular, etc., extension of each flange. However, projections 38,39 are not simply tapered tips of the flanges, since they flex relatively independently of the flanges. At its outer edge, a projection preferably will not extend beyond the outer edge of the flange from which it extends. That is, the leading edge of projection 38, i.e., the edge that is perpendicular to the inner surface 42 of the syringe barrel 12 and thus which defines syringe chamber 15, will not extend beyond and thus will be coincident with the leading edge of flange 32 or 34. Similarly, the trailing edge of projection 39, i.e., the edge that is perpendicular to inner surface 42, will not extend beyond and thus will be coincident with the trailing edge of flange 32 or 34. Flanges 32 and 34 are identical except for their relative positions on gasket 14, i.e., they are mirror images of each other. As shown, the first and second flanges 32 and 34 define an annular space 36 intermediate the body portion 30 and the inner surface 42 of the barrel 12. While the boundary of each of flange 32 and 34 that defines space 36 is tapered up to projection 38 and 39, respectively, the point of juncture of projection 38 and flange 32 or projection 39 and flange 34 is angled rather than tapered, and preferably forms a 90 degree angle.

The exceedingly slight contact between projections 38,39 and inner surface 42 confers relatively low friction upon movement of the gasket 14 in the barrel 12, permitting relatively free movement of the plunger and gasket in the syringe barrel. Thus, the low resistance syringe embodiment of the present invention may be utilized in special medical procedures, where free movement of the syringe plunger in the barrel is required, previously accomplished by precision ground glass syringes. The syringe barrel 12 and plunger 13 may be made from relatively inexpensive substantially transparent plastic materials, such as polycarbonate, while the syringe gasket 14 may be constructed from inexpensive elastomers, such as polyisoprene rubber. Thus, syringes of the present invention may be constructed in a simplified manner from inexpensive parts, while accomplishing results of relatively expensive ground glass syringes. Any size syringe may be used according to the invention, e.g., 50 cc, 20 cc, 10 cc, or 1.0 cc syringes, or any other conventional size.

In use, a syringe of the invention may be applied to, e.g., needle aspiration procedures, e.g., thoracentesis, wherein fluid is removed from the body. It is necessary for the physician to locate the pleural space without piercing the lung or other vital organs. A thin needle of about 16 gauge and on the order of five inches in length is attached to hub 20 of the syringe. The aspirating device 10 is preliminarily arranged with the plunger 13 positioned well within barrel 12 by applying pressure to thumb-receiving end 16 and thus pressing spring 40 into a tighter coil. With one hand, the needle 11 is inserted into the chest wall or back toward the pleural space. Upon insertion of the needle into the body tissue, a vacuum is created within the syringe barrel 12. Location of the pleural space is evidenced by the partial release of this vacuum due to automatic aspiration of pleural fluid into the syringe barrel 12. Any pressure which has been maintained on the thumb-receiving end of the plunger 13 of the device 10 is relieved, thus allowing spring 40 to be released as the partial vacuum is relieved by flow of pleural fluid into the barrel 12. If the pleural fluid is completely removed without fully releasing the vacuum within barrel 12, pressure may then be again applied to thumb-receiving end 16 of plunger 13 in order to prevent further movement of plunger 13 out of barrel 12 during withdrawal of the needle from the body. This neutralizes the pressure within the syringe barrel 12 and allows the aspirate in the barrel 12 to remain in the barrel 12 while the needle is withdrawn from the patient. The aspirated fluid may then be expelled from the syringe barrel 12 by forcing the plunger 13 downwardly into the barrel by applying pressure to thumb-receiving end 16 and against the bias of spring 40. Thus, precise control of the termination of negative pressure during fluid removal can be achieved.

Thus, also according to the invention, wherein a low friction syringe is used, the syringe gasket 14 provides an effective seal for exceedingly delicate and smooth pumping and aspirating of fluid during such sensitive procedures as locating the epidural space or administering spinal anesthesia.

During forward pumping movement of the syringe plunger 13 in the barrel 12, projections 38,39 provide an effective seal for the gasket 14 during pumping of fluids out of the syringe chamber. When the syringe plunger is urged outward by the biasing means in a rearward direction in the barrel 12, during aspiration of fluids, the smooth sliding action effected by the sliding of projections 38,39 against the inner surface 42 of the syringe barrel 12 allows for smooth withdrawal movement of the syringe plunger 13 as it slides along the inner surface 42 of barrel 12. In this manner, the gasket 14 permits aspiration of fluids into the syringe chamber 15.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

I claim:
1. An aspirating syringe, comprising;
  (a) a plastic syringe barrel having an exterior wall and an inner surface, and a leading and a trailing end, said inner surface and said ends defining a hollow interior chamber and a predetermined volume, said leading end having an opening extending through a hub, said trailing end terminating at an outer rim;
  (b) a plastic plunger operative in said barrel through said barrel trailing end to define said hollow interior chamber and said predetermined volume, said plunger extending longitudinally within and beyond said barrel leading end and being movable in said barrel inwardly toward said leading end and outwardly away from said leading end, thereby varying the volume of said barrel interior chamber, said plunger having a sealing end receivable inside said barrel to substantially seal said hollow interior chamber and a thumb-receiving end outside said barrel, wherein said plunger sealing end comprises an elastomeric gasket comprising a body with forward and rearward ends and first and second annular flanges positioned circumferentially at the forward and rearward ends of the body, the flanges being separated by an annular space intermediate the body portion and the barrel inner surface, wherein the gasket further comprises an annular projection extending from each flange, each projection being of reduced thickness relative to the thickness of each flange and providing a contact point with the barrel inner surface when said plunger sealing end is received in said barrel chamber, thereby enabling low friction between said gasket and said barrel inner surface during forward and rearward movement of said gasket; and (c) an outward biasing means coiled around said plunger between said barrel trailing end and said plunger thumb-receiving end to bias the plunger outwardly from the syringe barrel upon advancement of the plunger into said barrel.

2. The aspirating syringe of claim 1, said outward biasing means comprising a spring.

3. A method of aspirating a bodily specimen, comprising providing the syringe of claim 1 in operative association with a needle and arranged with pressure applied to the thumb-receiving end of the syringe such that the plunger is positioned well within the barrel;

inserting the needle into a patient;

relieving sufficient pressure on the thumb-receiving end to allow the syringe plunger to retract sufficiently to aspirate a specimen from the patient into the needle; and removing the needle from the patient.

4. The method of claim 3, further comprising re-applying sufficient pressure to the thumb-receiving end of the syringe to eject the specimen from the needle.

5. The aspirating syringe of claim 1, further comprising a finger grip member extending perpendicular from said barrel trailing end.

* * * * *